(12) United States Patent
Shaw (10) Patent No.: US 6,770,297 B1
(45) Date of Patent: Aug. 3, 2004

(54) CONTROLLED RELEASE DELIVERY SYSTEM OF SOLID DOSAGE FORM

(75) Inventor: Jiajiu Shaw, Ann Arbor, MI (US)

(73) Assignee: Unitech Pharmaceuticals, Inc., Ann Arbor, MI (US)

( * ) Notice: Subject to any disclaimer, the term of this patent is extended or adjusted under 35 U.S.C. 154(b) by 218 days.

(21) Appl. No.: 09/580,232

(22) Filed: May 26, 2000

(51) Int. Cl.⁷ .......................... A61K 9/24; A61K 9/20; A61K 9/30; A61K 9/36; A61K 9/32
(52) U.S. Cl. .................... 424/473; 424/464; 424/468; 424/471; 424/472; 424/475; 424/479; 424/482
(58) Field of Search .................. 424/464, 468, 424/471, 472, 473, 475, 479, 482

(56) References Cited

U.S. PATENT DOCUMENTS 5,186,942 A * 2/1993 Deters et al. ............... 424/473
5,200,194 A * 4/1993 Edgren et al. .............. 424/473
6,004,582 A * 12/1999 Faour et al. ................ 424/473

OTHER PUBLICATIONS

"Ditropan" Physician's Desk Reference, Edition 54, 2000, ISBN No. 1–56363–330–2, 2000, Medical Economics Co., Inc. Montvale, NJ 07645–1742.*

"Glucotrol XL", XL Physician's Desk Reference, Edition 54, 2000, ISBN No. 1–56363–330–2, 2000, Medical Economics Co., Inc. Montvale, NJ 07645–1742.*

"Ditropan®", Physicians' Desk Reference, Edition 54, 2000, ISBN No. 1–56363–330–2, ©2000, Medical Economics Co., Inc. Montvale, NJ 07645–1742.

"Glucotrol XL®", XLPhysicians' Desk Reference, Edition 54, 2000, ISBN No. 1–56363–330–2, ©2000, Medical Economics Co., Inc. Montvale, NJ 07645–1742.

* cited by examiner

Primary Examiner—Thurman K. Page
Assistant Examiner—S. Tran
(74) Attorney, Agent, or Firm—Brinks Hofer Gilson & Lione; Gregory H. Zayia (57) ABSTRACT

This invention relates to a controlled release delivery system of solid dosage form with a plurality of controls on the release of the active ingredient or ingredients.

19 Claims, 6 Drawing Sheets

A. Vertical Cross Section

B. Horizontal cross Section

1. membrane of the main compartment
2. composition on the inside of the main compartment
3. membrane of a sub-compartment
4. composition on the inside of a sub-compartment
5. membrane of a sub-compartment
6. composition on the inside of a sub-compartment
7. composition coated on the outside of the membrane of the main compartment
8. composition coated on the outside of the membrane of a sub-compartment Fig. 1 (drawing for Example 3)

A. Vertical Cross Section

B. Horizontal cross Section

1. membrane of the main compartment
2. composition on the inside of the main compartment
3. membrane of a sub-compartment
4. composition on the inside of a sub-compartment
7. composition coated on the outside of the membrane of the main compartment Fig. 2 (drawing for Example 6)

A. Vertical Cross Section

B. Horizontal cross Section

1. membrane of the main compartment
2. composition on the inside of the main compartment
3. membrane of a sub-compartment
4. composition on the inside of a sub-compartment
5. membrane of a sub-compartment
6. composition on the inside of a sub-compartment
7. composition coated on the outside of the membrane of the main compartment
8. composition coated on the outside of the membrane of a sub-compartment Fig. 3 (drawing for Example 7)

A. Vertical Cross Section

B. Horizontal cross Section

1. membrane of the main compartment
2. composition on the inside of the main compartment
5. membrane of a sub-compartment
6. composition on the inside of a sub-compartment
7. composition coated on the outside of the membrane of the main compartment
9. membrane of a sub-compartment
10. composition on the inside of a sub-compartment Fig. 4 (drawing for Example 10)

A. Vertical Cross Section

B. Horizontal cross Section

1. membrane of the main compartment
2. composition on the inside of the main compartment
7. composition coated on the outside of the membrane of the main compartment
5. membrane of a sub-compartment
6. composition on the inside of a sub-compartment
8. composition coated on the outside of the membrane of a sub-compartment Fig. 5 (drawing for Example 11)

A. Vertical Cross Section

B. Horizontal cross Section

1. membrane of the main compartment
2. composition on the inside of the main compartment
3. membrane of a sub-compartment
11. inner composition on the inside of a sub-compartment
12. outer composition on the inside of a sub-compartment Fig. 6 (drawing for Example 12)

A. Vertical Cross Section

B. Horizontal cross Section 1. membrane of the main compartment
2. composition on the inside of the main compartment
5. membrane of a sub-compartment
6. composition on the inside of a sub-compartment

CONTROLLED RELEASE DELIVERY SYSTEM OF SOLID DOSAGE FORM

FIELD OF INVENTION

This invention relates to a controlled release delivery system of solid dosage forms with a plurality of controls on the release of the active ingredient or ingredients.

BACKGROUND OF THE INVENTION

Controlled release delivery systems have been of interest to many researchers, especially in pharmaceutical industry. Controlled release includes slow release or programmed release. There are several advantages in using controlled release dosage forms. For instance, a patient may need to take certain tablet three times a day. With a slow release dosage form, the patient may only need one tablet a day. Another example is that enteric-coated tablets are useful to protect the active ingredient against gastric fluid and release the active ingredient only in the intestine.

In pharmaceutical of solid dosage form, there have been many different versions of controlled release systems. More popular controlled systems are matrix system, membrane controlled system, membrane controlled with one or more orifices. Membrane controlled delivery systems developed by Alza pharmaceutical are becoming more popular. Tegretol®-XR (by Novartis Pharmaceuticals) and Procardia XR® (by Pratt Pharmaceutcals, Division of Pfizer) are two examples of controlled release products made by Alza's membrane controlled system.

Drug release in a membrane system is basically controlled by osmotic pressure due to the concentration gradient. The matrix system also uses concentration gradient except the active ingredient is blended or waged in the polymer matrix. All of these systems are basically controlled by one major driving force.

One of the outstanding controlled release system, different from the above systems, is sometimes called a "push-pull" system also developed by Alza Pharmaceutical (U.S. Pat. No. 5,091,190 Feb. 25, 1992). In this system, there are two compositions in a lumen, one contains the active ingredient and the other contains a hydrogel. The two compositions are arranged in a two-layered format and coated by a membrane, wherein an orifice is made only on one side, the side with composition containing active ingredient. One representative example is Glucotrol XR® (by Pratt Pharmaceuticals, Division of Pfizer). This prior art has two driving forces to release the active ingredient: (1) the water penetrating through the membrane swells or dissolve both compositions, generating osmotic pressure in the lumen and push the composition out through the orifice, and (2) the water in the lumen swells the hydrogel, which expands and push other composition out through the orifice on the other side of the coated tablet.

There are several problems with this push-pull system. First, the membrane must have one or more than one orifices usually drilled by an expensive laser drill or other mechanical drill. Secondly, the orifices must be made on the particular side of the tablet. Otherwise the delivery system will not function properly. Therefore, additional process is needed to arrange the tablets in the specific orientation before the tablets can be drilled. Thirdly, some of the active might be waged into the hydrogel as the hydrogel is swollen, thus, increasing the complexity in the development of the dosage form. Yet another potential problem is that both compositions are directly contacting the same membrane, therefore swelling of the hydrogel starts immediately, and it may be difficult to achieve a delayed release profile. In other words, the two driving forces start at about the same time.

This invention is particularly designed to improve the current delivery systems for solid dosage forms, especially the push-pull system in U.S. Pat. No. 5,091,190. The delivery system in this invention does not need to be drilled, thus, saving time and reducing costs. The delivery system in this invention does not have a direct contact between any two compositions because of the additional membrane in between, thus, easier to develop. Different from the Push-Pull system, which consists of two compositions in a membrane, this invention comprises a compartment-in-compartment design. In this invention, the main compartment is confined by a membrane, and the sub-compartment or sub-compartments inside the main compartment, are also confined by a membrane. This design makes the delivery system more versatile than any known prior arts.

In addition to the above advantages, this invention has a plurality of controls in releasing the drug composition or compositions. The driving force for each control can be initiated at different point of time. Therefore, this invention is more flexible and more versatile in developing a controlled release dosage form suitable for a variety of situations.

SUMMARY

Unlike most controlled release system, where the release of drug composition or compositions is primarily controlled by one or two driving forces, the delivery system in this invention may comprise a plurality of controls on the release of drug composition or compositions.

Unlike a push-pull system, wherein both of the two compositions are confined in a membrane, i.e., in one compartment, the delivery system in this invention comprises one main compartment and one or a plurality of sub-compartments. Unlike a Push-Pull system, wherein there are two compositions, with the active in active ingredient in one composition and hydrogel in the other composition, this invention comprises one or more than one active ingredients in each of the compartments (main compartment or individual sub-compartment). Yet another important aspect of this invention is that it comprises different kinds of driving forces and these driving forces may be initiated at different points in time. Therefore, this invention discloses a superior delivery system suitable for the development of controlled release solid dosage forms.

DETAILED DESCRIPTION OF THE PRESENTLY PREFERRED EMBODIMENTS

This invention discloses a controlled release delivery system for solid dosage forms. Said delivery system comprises the following components:

1. A Main Compartment

The main compartment is confined by a membrane, which comprises one of the following:

a. a microporous membrane, or b. an enteric-coating membrane

Said microporous membrane comprises pharmaceutically acceptable polymeric membrane that releases drug by diffusion through the micropores (1) within the membrane itself, or (2) formed by the inclusion, within the membrane, of various water-soluble or water-swellable excipients that may be subsequently leached out.

Said membranes includes, but not limited to cellulose ester, cellulose ether, cellulose ester-ether, acrylic acid polymer, acrylic acid co-polymer, polyvinyl acetate, and silicon polymer.

Said water-soluble or water-swellable excipients include, but not limited to, sodium chloride, citric acid, glucose, fructose, sucrose, dextrose, lactose, malic acid, mannitol, and ethylene glycol.

Said enteric-coating membrane comprises membrane that remains intact in the stomach but breaks down readily in the small intestine where the pH is much higher than the pH in the stomach. Enteric coating membrane includes, but not limited to, hydroxypropyl methylcellulose phthalate, hydroxypropyl methylcellulose acetate succinate, polyvinyl acetate phthalate, cellulose acetate trimellitate, cellulose acetate phthalate, poly(methacrylic acid-ethylacrylate), and poly(methacrylic acid-methyl methacrylate).

The inside of the main compartment comprises a pharmaceutical composition comprising one or more of the following: active ingredient, osmotic agent, pharmaceutically acceptable excipients, hydrogel, and the combination thereof. In addition, the inside of the main compartment also comprises at least one sub-compartment described in the next paragraph.

2. One or a Plurality of Sub-compartments

There is one or a plurality of sub-compartment on the inside of the main compartment. Said sub-compartment is confined by a mircoporous membrane. Said microporous membrane comprises pharmaceutically acceptable polymeric membrane that releases drug by diffusion through the micropores (1) within the membrane itself, or (2) formed by the inclusion, within the membrane, of various water-soluble or water-swellable excipients that may be subsequently leached out.

Said microporous membranes includes, but not limited to cellulose ester, cellulose ether, cellulose ester-ether, acrylic acid polymer, acrylic acid co-polymer, polyvinyl acetate, and silicon polymer.

Said water-soluble or water-swellable excipients include, but not limited to, sodium chloride, citric acid, glucose, fructose, sucrose, dextrose, lactose, malic acid, mannitol, and ethylene glycol.

The inside of the sub-compartment comprises a pharmaceutical composition comprising one or more of the following: active ingredient, osmotic agent, hydrogel, other pharmaceutically acceptable excipients, and the combination thereof 3. An Optional Erodable Outer Layer on the Membrane of the Main Compartment Optionally, an erodable outer layer may be coated on the membrane of the main compartment; the outer layer comprises a pharmaceutical composition comprising an active ingredient, suitable pharmaceutical excipients, or the combination thereof.

4. An Optional Erodable Outer Layer on the Membrane of the Sub-compartment or Sub-compartments Optionally, an erodable outer layer may be coated on the membrane of the sub-compartment; said outer layer comprises a pharmaceutical composition comprising an active ingredient, suitable pharmaceutical excipients, or the combination thereof.

The general mechanism for the release of the desired drug composition or compositions may be described as follow:

(A) When the Main Compartment is Surrounded by a Microporous Membrane

In this case, the membrane may serve as the primary control for the release of the desired drug composition or composition. Imbibing fluid into the main compartment causing the composition or compositions in the main compartment to provide a dispensable aqueous composition and delivered through the microporous membrane out of the dosage form.

At a later stage, when less drug-composition or compositions are available in the main compartment, more water becomes available in the main compartment. At this stage, water begins to be imbibed into the sub-compartment through the microporous membrane confining the sub-compartment or sub-compartments. This has several effects on the drug release. Three of the effects are listed as follow:

1. Water imbibing into the sub-compartment, which comprises a water-soluble excipient, can help reduce the amount of water in the main compartment, thus, providing a secondary driving force for the main compartment to imbibe more water into the main compartment, thus, providing supplementary driving force to further release the drug composition out of the main compartment.

2. Water imbibing into the sub-compartment, which comprises a pharmaceutically acceptable hydrogel, can cause the volume of a sub-compartment to expand, thus, help push the desired composition or compositions in the main compartment out of the dosage form.

3. Water imbibes into a sub-compartment, comprising a drug composition, can provide a dispensable aqueous drug composition and delivered out of the sub-compartment into the main compartment; this drug composition, be it the same or different from that in the main compartment, is later pushed out of the main compartment by diffusion.

(B) When the Main Compartment is Surrounded by an Enteric-coating Membrane

The membrane may serve as the primary control for delaying the release of drug composition or compositions in the main compartment. The enteric-coating membrane stays intact in the stomach and hold the contents in the membrane until it is reaching the intestine. At that point of time, the contents in the main compartment are released; this includes the drug composition in the main compartment and the sub-compartment or sub-compartments. The composition in the main compartment may be readily released as the main membrane break up. However, the contents in the sub-compartment or sub-compartments will be released in a controlled manner by the membrane on the sub-compartment or sub-compartments.

The optional outer layer on the main compartment can serve for different purposes. For instance, if an immediate bolus dose is needed, a drug composition may be coated on the outside of the membrane for an immediate release of the bolus dose. Another case is that if a delay is required before the drug is released, an outer coating with pharmaceutically acceptable polymeric excipients, such as hydroxypropylmethylcellulose (HPMC), may be coated by standard pharmaceutical technique.

The optional outer coating on the sub-compartment membrane serves as an additional sub-control for the release of active ingredient or ingredients. In this case, the water molecules dissolve and/or swell this outer coating before penetrating through the membrane of the sub-compartment. Another case is that an active ingredient may be coated on the outside of the sub-compartments as a second-stage supply of the active ingredient.

Pharmaceutical colors may be blended in the membrane or in the composition or compositions in this invention.

Several examples are as listed as follow:

EXAMPLE 1

A System with One Sub-compartment

The main compartment comprises a pharmaceutical composition, which comprises an active ingredient and pharmaceutical excipients; the main compartment is coated by a membrane such as cellulose acetate with suitable amount of ethylene glycol.

The main compartment also comprises one sub-compartment in the main compartment; the sub-compartment is coated by membrane such as cellulose acetate; the sub-compartment comprises an osmotic agent such as NaCl on the inside.

Method of making the system: Using standard technique to make tablets out of NaCl (add suitable amount of lubricant if necessary); coat the NaCl tablets by standard technique; embed a coated NaCl tablet into a pharmaceutical blend comprising suitable excipients and an active ingredient and make a tablet-in-a-tablet; coat the final tablet with cellulose acetate by standard technique to obtain the finished product.

EXAMPLE 2

A System with One Sub-compartment

A system, which is the same as in EXAMPLE 1 except that instead of NaCl, a pharmaceutically acceptable hydrogel is in the sub-compartment. In this example, polyethylene oxide with molecule weight of 4,000,000 to 8,000,000 is used in this sub-compartment.

EXAMPLE 3

Figure 1:
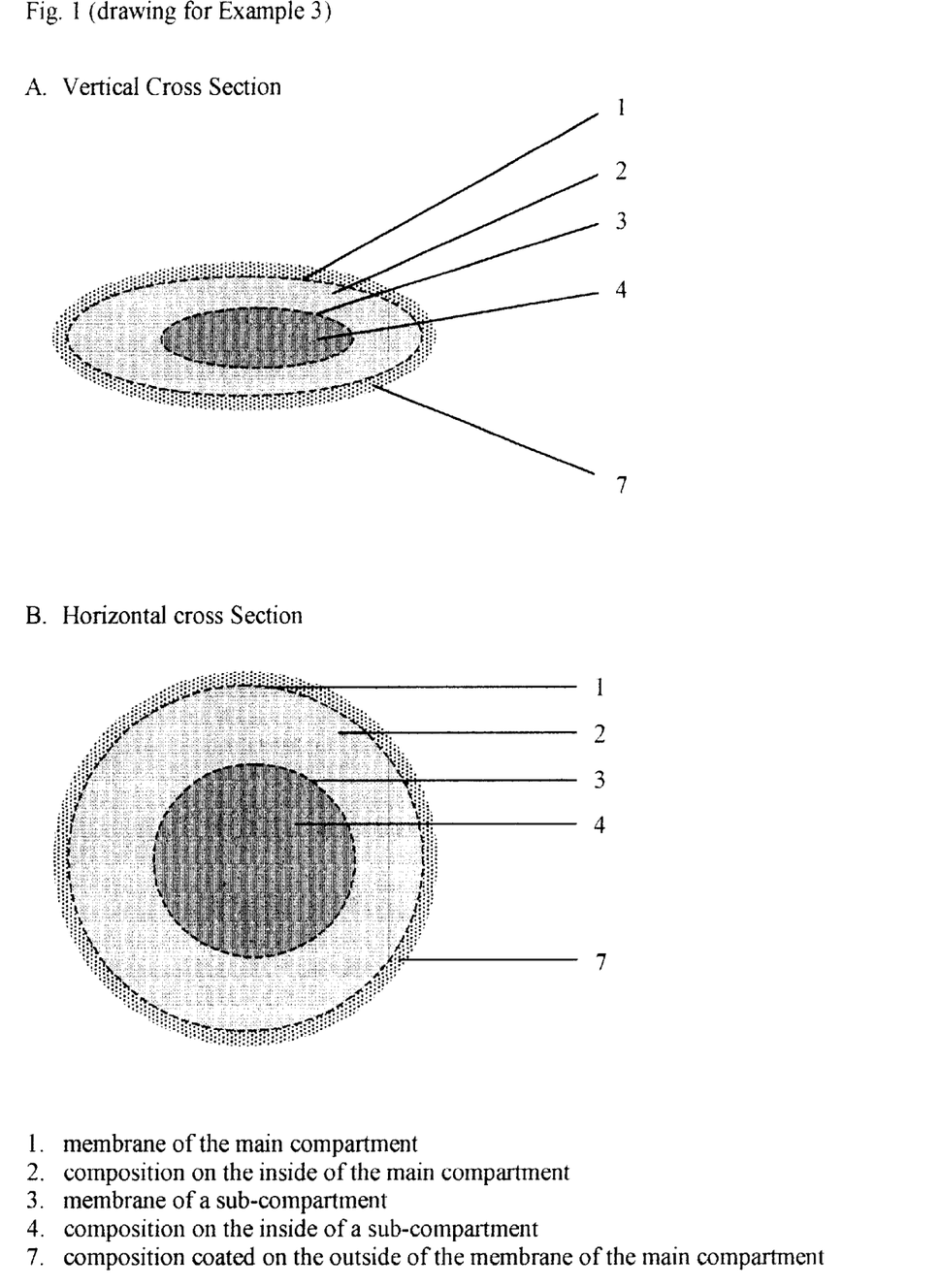
FIG. 1 shows vertical and horizontal corss-sectional views of a system with one sub-compartment and ana outer coating on the outside of the membrane of the main compartment.

A system with One Sub-compartment and an Outer Coating on the Outside of the Membrane of the Main Compartment (FIG. 1)

Using standard pharmaceutical coating technique, coat the outside of the main compartment membrane in EXAMPLE 2 by an immediate release composition comprising the active ingredient so that the active ingredient is immediately released before the membrane-controlled release starts. Standard pharmaceutical technique is used to make the tablets.

EXAMPLE 4

A System with a Plurality of Sub-compartments

Main compartment is coated by membrane, such as polyvinyl acetate with suitable amount of ethylene glycol, and the inside of the main compartment comprises an active ingredient and pharmaceutical excipients.

In side the main compartment, there is a plurality of membrane coated NaCl pellets randomly distributed. The NaCl pellets are coated with cellulose acetate.

Method of making the tablets: Coated NaCl pellets are commercially available. Use standard pharmaceutical technique for the following process. Blend these coated NaCl pellets with suitable pharmaceutical excipients and an active ingredient; compress and make tablets; coat the final tablets to make the finished product.

EXAMPLE 5

A System with Two Different Types of Sub-compartments

Main compartment comprises an active ingredient and pharmaceutical excipients. Main compartment is coated by membrane such as cellulose acetate with suitable amount of ehtylene glycol.

In the main compartment, there are two types of sub-compartments; a plurality of sub-compartments, coated NaCl pellets, and one sub-compartment containing hydrogel, such as polyethylene oxide. Both types of sub-compartments are coated by cellulose acetate.

Method of making the system: Using standard technique to perform the following process. Make tablets out of hydrogel, such as polyethyolene oxide (add suitable lubricant if necessary); coat the hydrogel tablets with cellulose membrane by standard technique; embed one coated coated hydrogel tablet into a blend comprising (1) suitable excipients (2) an active ingredient, and (3) a plurality of coated NaCl pellets; make a tablet-in-tablet; coat the final tablet cellulose acetate with suitable amount of ehtylene glycol to obtain the finished product.

EXAMPLE 6

Figure 2:
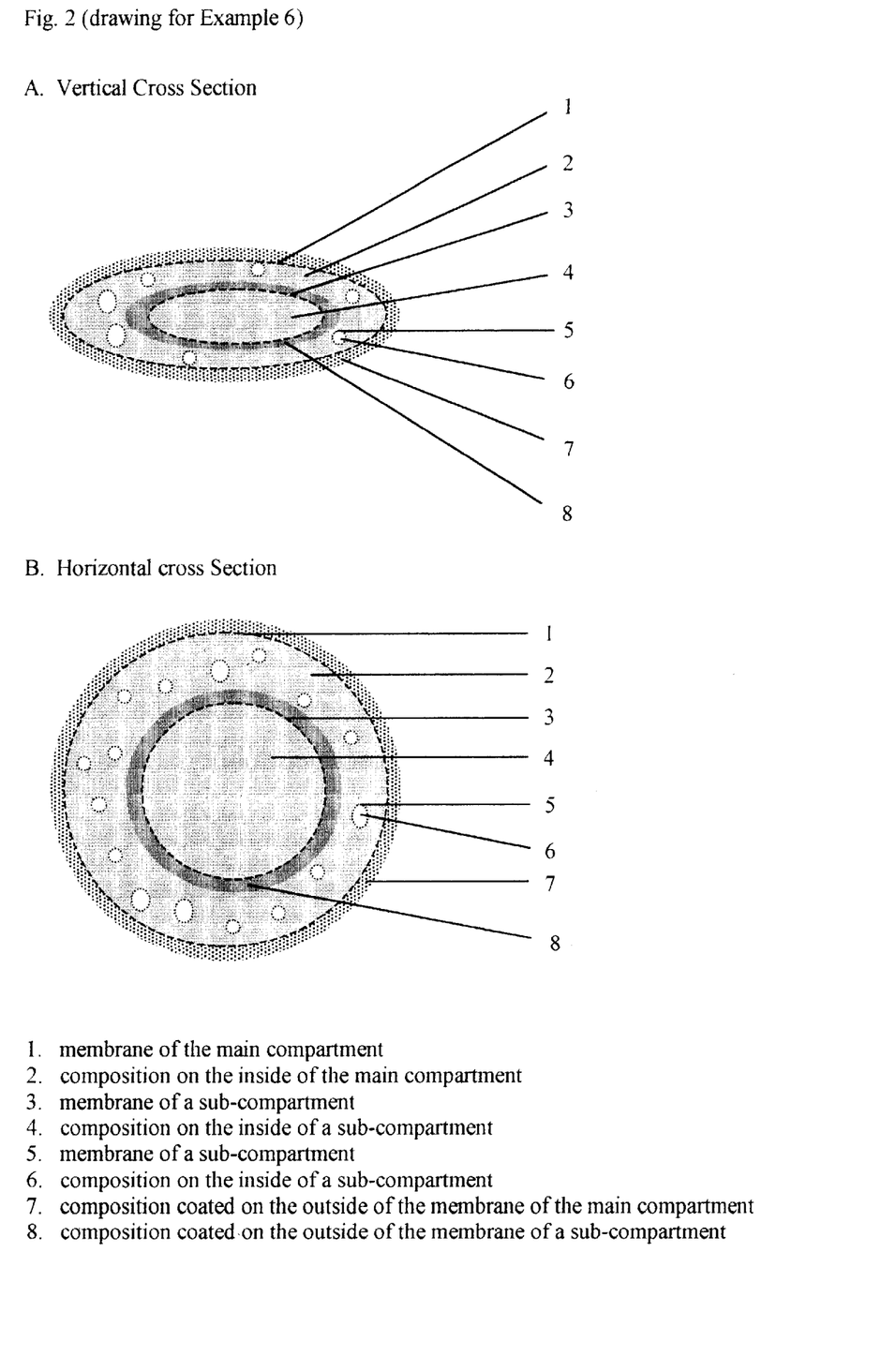
FIG. 2 shows vertical and horizontal cross-sectional views of a system having an over-coat on the membrane of the main compartment and having two different types of sub-compartments.

A System Having an Over-coat on the Membrane of the Main Compartment and having Two Different Types of Sub-compartments (FIG. 2)

Using standard pharmaceutical coating technique, coat the outside of the main compartment membrane in EXAMPLE 5 by an immediate release formulation comprising the active ingredient so that an immediate release is realized before the membrane-controlled release starts. Standard pharmaceutical technique is used to make the tablets.

EXAMPLE 7

Figure 3:
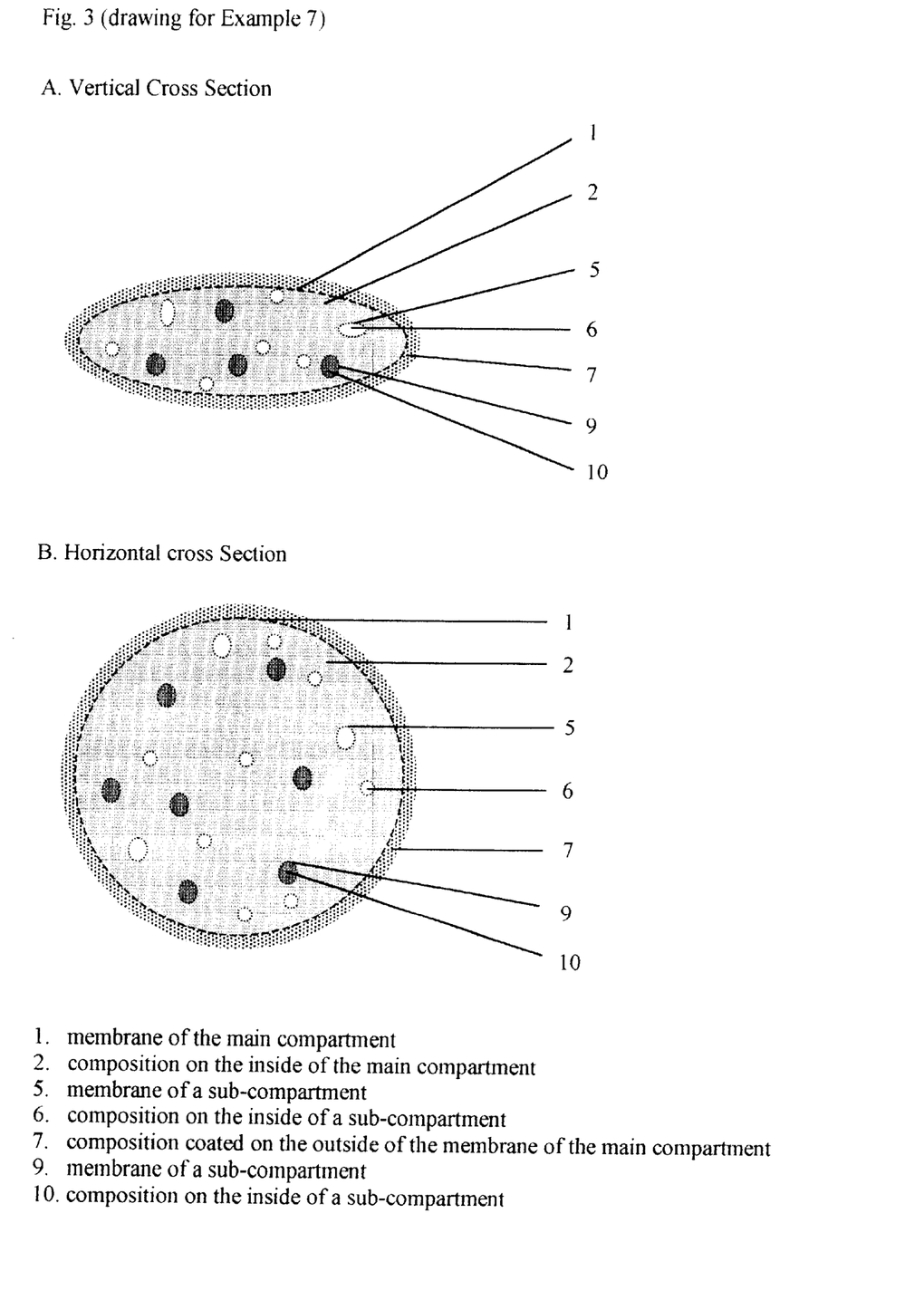
FIG. 3 shows vertical and horizontal cross-sectional views of a system with an over-coating on the main compartment and the sub-compartments.

A System with Over-coating on the Main Compartment and the Sub-compartments (FIG. 3)

A system, which is the same as in EXAMPLE 4 except an over coat is on the membrane of the main compartment and the sub-compartment. The overcoat is a pharmaceutical composition comprising an active ingredient and customary pharmaceutical excipients.

EXAMPLE 8

A System with Two Active Ingredients in the Main Compartment

The main compartment comprises two different active ingredients and customary pharmaceutical excipients; the main compartment is coated by cellulose acetate.

Inside the main compartment, there is a plurality of sub-compartment comprising NaCl coated by cellulose acetate.

Method of preparation: Standard pharmaceutical technique is used to prepare a blend comprising two active ingredients and suitable excipients. Add the coated NaCl pellets in the blend and mix well. Compress and make the finished tablets.

EXAMPLE 9

A System with Two Active Ingredients, One in the Main Compartment and the Other in the Sub-compartment A system, which is the same as in EXAMPLE 1 except that the sub-compartments comprise a pharmaceutical composition comprising at least an active ingredient, which is different from that out of the sub-compartments and in the main compartment.

EXAMPLE 10

Figure 4:
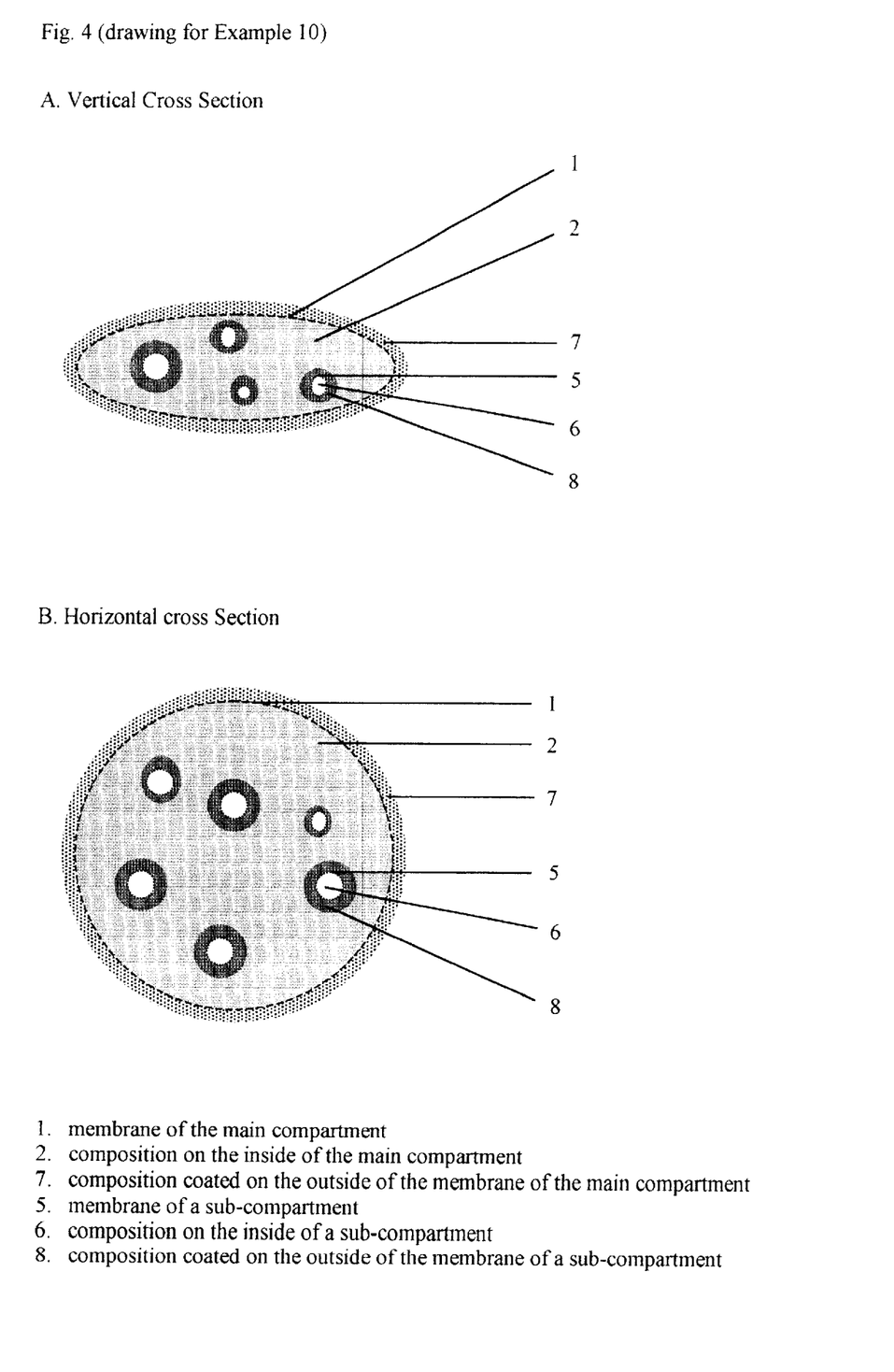
FIG. 4 shows vertical and horizontal cross-sectional views of a system with two different types of sub-compartments.

A System with Two Different Types of Sub-compartments (FIG. 4)

A system which is the same as in EXAMPLE 5 except that there is a plurality of units for both types of sub-compartments inside the main compartment.

EXAMPLE 11

Figure 5:
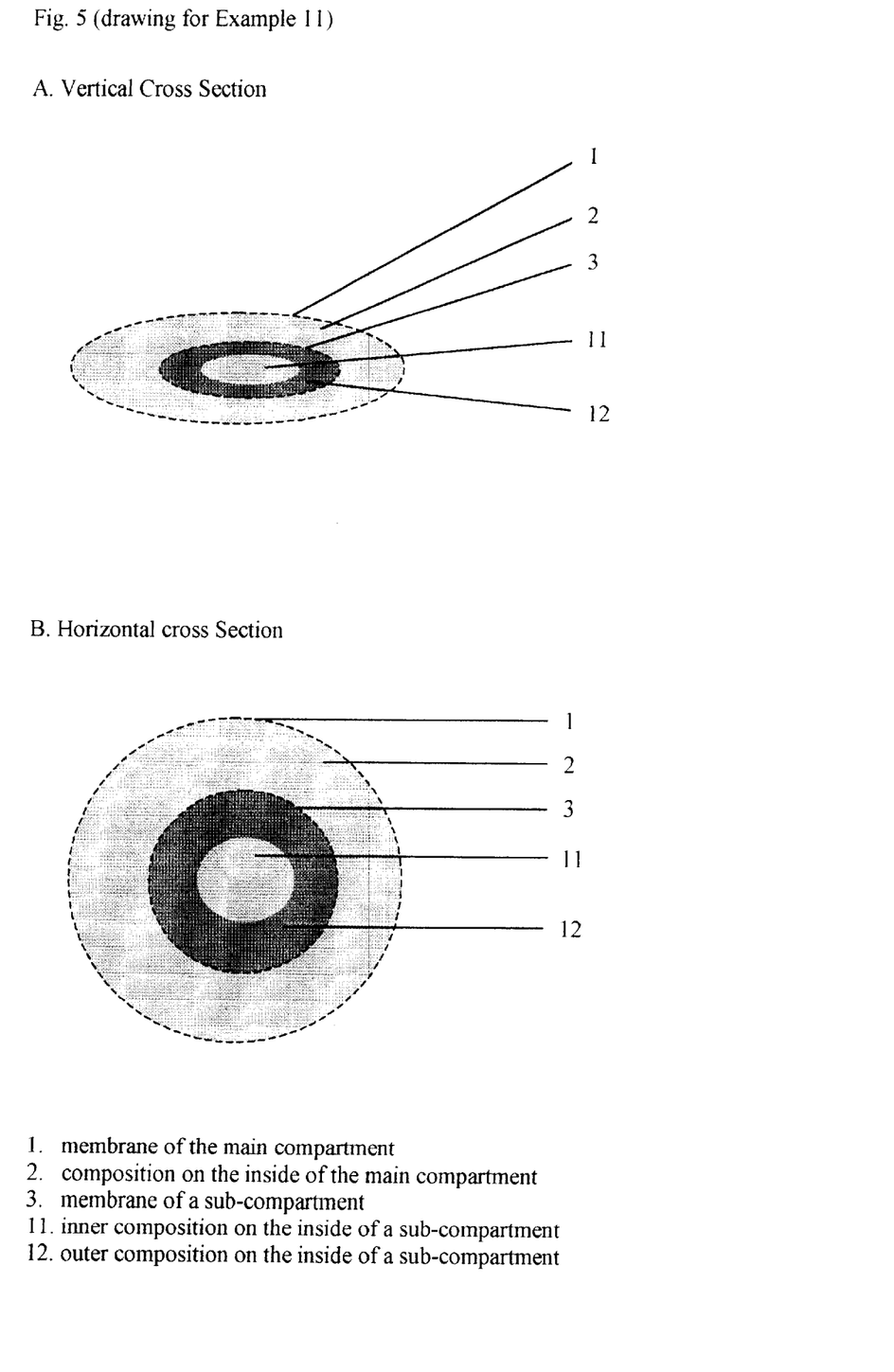
FIG. 5 shows vertical and horizontal cross-sectional views of a two-compartment system with two active ingredients.

An Example of a 2-compartment System with Two Active Ingredients (FIG. 5)

Main compartment comprises a pharmaceutical composition comprising an active ingredient and customary pharmaceutical excipients. The main compartment is coated by cellulose acetate.

Main compartment also comprises a sub-compartment. Said sub-compartment, coated with cellulose acetate, comprises a table-in-tablet. The inner tablet, comprising a hydrogel, is on the inside of an outer tablet which comprises a pharmaceutical composition comprising an active ingredient same as that between the main-compartment membrane and the sub-compartment membrane.

EXAMPLE 12

Figure 6:
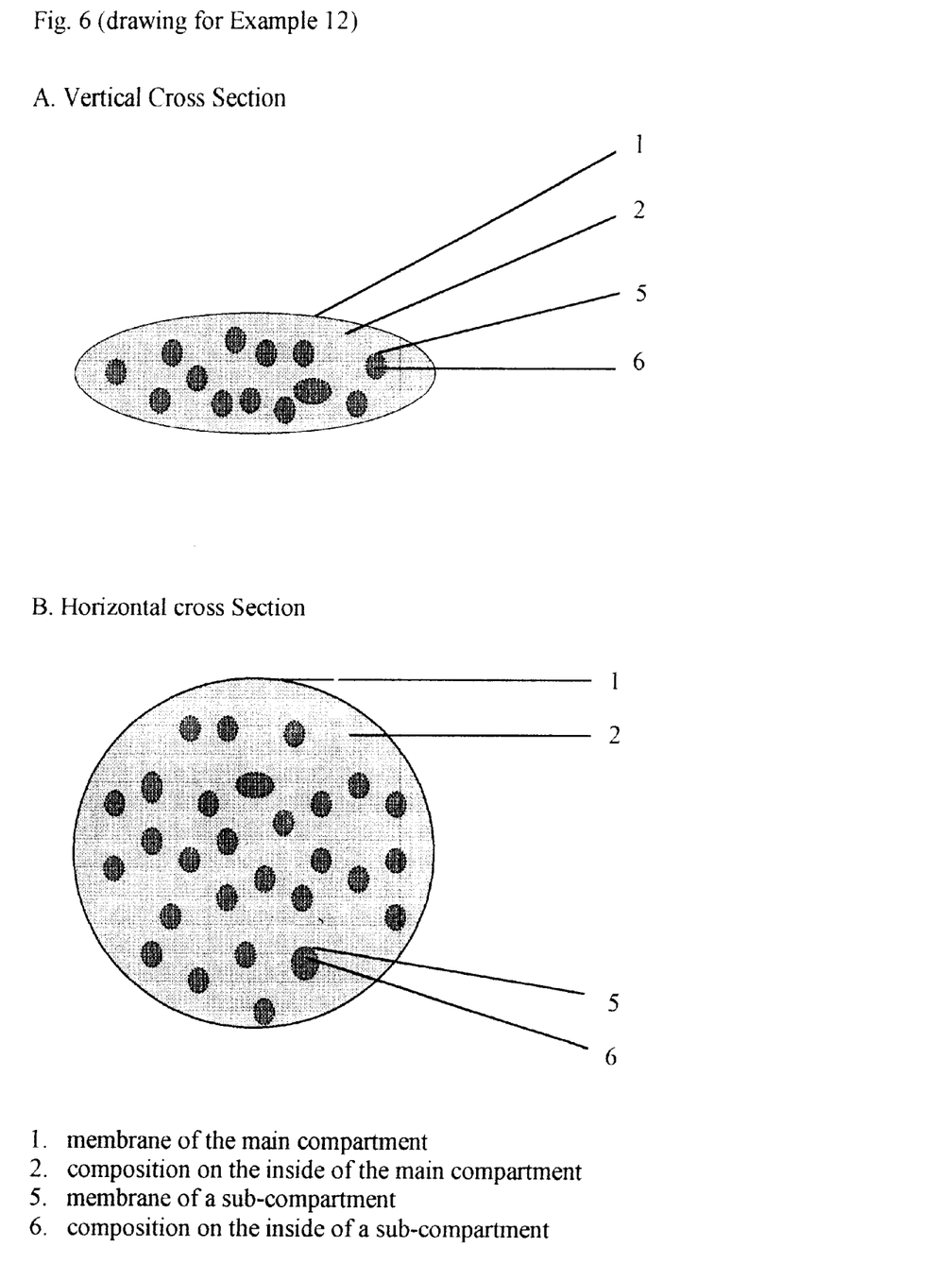
FIG. 6 shows vertical and horizontal cross-sectional views of a two-compartment system and two drug compositions with a delayed release mechanism.

An Example of a 2-compartment System and 2 Drug Compositions with Delayed Release Mechanism (FIG. 6)

In this dosage form, there is a drug composition in the main compartment and the other in a plurality of sub-compartments. The main compartment is coated by an enteric coating membrane. As the dosage form is administered, the enteric coating membrane remains intact in the stomach. As the dosage form goes to the intestine, the enteric coating membrane breaks up and release the drug composition in the main compartment. At about the same time, the multiple sub-compartments are spread into the intestine. As water imbibe into the sub-compartments, the drug composition in these sub-compartment begins to be released through the microporous membrane.

EXAMPLE 13

A System with One Active Ingredient

As in EXAMPLE 12, when the drug active ingredient in the main compartment and that in the sub-compartments are the same. In this case, the active ingredient is not released in the stomach and delayed until the system is in the small intestine. As the system reaches the small intestine, there is a immediate release and there is also a slow release of the same active ingredient.

EXAMPLE 14

A System with Three Active Ingredients

An outer coating is on the outside of the membrane of the main compartment; said outer coating comprises a third active ingredient. The rest is the same as in EXAMPLE 12. In this case, one active ingredient will be release immediately, then a delay until the dosage form is in the stomach, then the second active ingredient is readily released and the third active ingredient is slowly

RAMIFICATION AND SCOPE

In conclusion, this invention comprises a controlled delivery system of solid dosage form, and the method of preparation.

Although the description above contains many specificities, these should not be construed as limiting the scope of the invention but as merely providing the illustrations of some of the presently preferred embodiments of this invention.

Thus, the scope of this invention should be determined by the appended claims and their legal equivalents, rather by the examples given.

What is claimed is:

1. A delivery system comprising the following:
   A main compartment confined by a pharmaceutically acceptable membrane, with the inside of the main compartment comprising (a) a pharmaceutical composition, and (b) one or a plurality of sub-compartments confined by membrane, which is porous or becomes porous upon contacting aqueous environment, with the inside of the sub-compartment or sub-compartments comprising a pharmaceutical composition, wherein the main compartment and the sub-compartment or compartments are independent of each other.

2. The delivery system in claim 1 wherein the composition in the main compartment and the composition in the sub-compartment, independently, comprise one or more of the following: active ingredient, osmotic agent, hydrogel, other pharmaceutically acceptable excipients, and the combination thereof.

3. The delivery system in claim 1 wherein the membrane is one of the following:
   a microporous membrane, or
   b. an enteric-coating membrane;
   wherein said microporous membrane comprises pharmaceutically acceptable polymeric membrane that releases drug composition by diffusion through (1) the micropores within the membrane itself, or (2) the micropores formed by the inclusion, within the membrane, of various water-soluble or water-swellable excipients that may be subsequently leached out;
   wherein said enteric-coating membranes are those that remain intact in the stomach but break down readily in the small intestine where the pH is much higher than the pH in the stomach.

4. The delivery system in claim 3 wherein the membrane of the main compartment and the membrane of the sub-compartment, independently, comprise pharmaceutically acceptable polymer or polymer blend.

5. The system in claim 1 wherein the composition in the main compartment comprises two different active ingredients.

6. The system in claim 1 wherein an outer layer is coated on the membrane of the main compartment, wherein said outer layer is a pharmaceutical composition comprising one or more of the following: active ingredient, osmotic agent, hydrogel, other pharmaceutically acceptable excipients, and the combination thereof.

7. The system in claim 1 wherein an outer layer is coated on the membrane of the sub-compartment or sub-compartments; said outer layer is a pharmaceutical composition comprising one or more of the following: active ingredient, osmotic agent, hydrogel, other pharmaceutically acceptable excipients, and the combination thereof.

8. The system in claim 1 wherein an outer layer is coated on the membrane of the main compartment and, independently, an outer layer is coated on the sub-compartment or sub-compartments, wherein said outer layer is independently a pharmaceutical composition comprising one or more of the following: active ingredient, osmotic agent, hydrogel, other pharmaceutically acceptable excipients, and the combination thereof.

9. The system in claim 1 wherein there is a single sub-compartment having one or more of the following on the inside of the sub-compartment: Active ingredient, hydrogel, osmotic agent, other pharmaceutically acceptable excipients, and the combination thereof.

10. The system in claim 9 wherein the single sub-compartment contains pharmaceutically acceptable polyethylene oxide.

11. The system in claim 10 wherein the polyethylene oxide has a molecular weight range of 1,000,000 to 10,000,000.

12. The system in claim 9 wherein the sub-compartment comprises NaCl on the inside.

13. The system in claim 1 wherein there is a plurality of sub-compartments and the sub-compartments comprise, independently, one or more of the following: Active ingredient, hydrogel, osmotic agent, other pharmaceutically acceptable excipients, and the combination thereof.

14. The system in claim 13 wherein the sub-compartments comprises NaCl on the inside.

15. The system in claim 13 wherein there are two types of sub-compartments each independently coated by a suitable membrane, and each independently containing one or more of the following: active ingredient, osmotic agent, hydrogel, other pharmaceutically acceptable excipients, and the combination thereof.

16. The system in claim 9 wherein the single sub-compartment comprises a two-composition tablet-in-tablet, wherein the composition of the inner tablet comprises a hydrogel and the surrounding composition comprises an active ingredient.

17. The system in claim 13 wherein said hydrogel is polyethylene oxide.

18. The system in claim 17 wherein said hydrogel has a molecular weight range of 1,000,000 to 10,000,000.

19. The system in claim 9 wherein the single sub-compartment comprises a two-composition tablet-in tablet, wherein the composition of the inner tablet comprises an osmotic agent and the surrounding composition comprises an active ingredient.

* * * * *